April 12, 1960 E. S. BOERNER Plant Pat. 1,931
CHRYSANTHEMUM PLANT
Filed Aug. 13, 1959
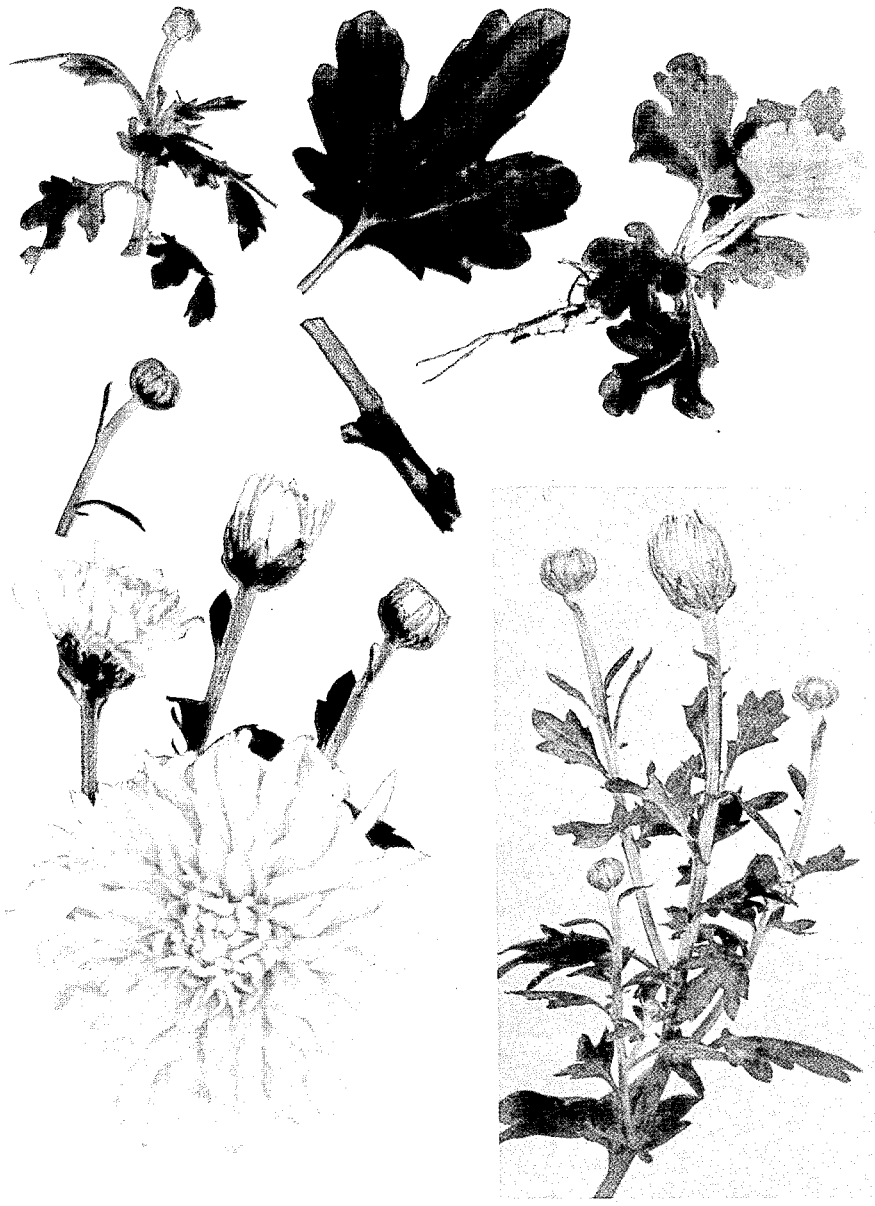
Inventor.
E. S. Boerner
By: Robb & Robb
Attorneys.

United States Patent Office

Plant Pat. 1,931
Patented Apr. 12, 1960

1,931

CHRYSANTHEMUM PLANT

Eugene S. Boerner, Newark, N.Y., assignor to Jackson & Perkins Company, Newark, N.Y., a corporation of New York Application August 13, 1959, Serial No. 833,658

1 Claim. (Cl. 47—60)

The present invention relates to a new and distinct variety of chrysanthemum plant of the decorative class, which was originated by me by crossing an unnamed and unpatented seedling derived from a cross of "Meadowlark" (Plant Patent No. 1,305) × "Thrust" (Plant Patent No. 1,168) with the variety known as "Martin" (Plant Patent No. 1,466).

The primary objective of this breeding was to produce a new chrysanthemum variety in which there is combined the early blooming habit and floriferousness of the parent variety "Martin" and the plant type and size of the unnamed seedling parent. This objective was fully achieved, along with other improvements, as evidenced by the following unique combination of characteristics which are outstanding in the new variety and which distinguish it from its parents, as well as from all other varieties of which I am aware:

(1) A low and compact habit of growth;
(2) A floriferous habit;
(3) An early blooming habit;
(4) A continuous blooming habit; and
(5) A distinctive orange general color tonality of the flowers.

Asexual reproduction of my new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black and white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, near the middle of September:

Parentage: An unnamed seedling of "Meadowlark" × "Thrust" × "Martin."
Classification: Decorative.
Growth: Compact; short.
Cold resistance: Hardy.
Blooming period: In the Newark, New York climatic area, the plants bloom continuously from about mid-September until frost.

*Flower*

Bud:
*Color.*—When sepals first divide—Ochraceous-Salmon, Plate 15. When petals begin to unfurl—Zinc Orange, Plate 15. When half-blown: inside of petals—Deep Chrome, Plate 3, lightly overcast with Cadmium Orange, Plate 3; outside of petals—Cadmium Yellow, Plate 3, lightly overcast with Orange, Plate 3.
*Peduncle.*—Color—Biscay Green, Plate 17. Strength—strong.

Bloom:
*Size.*—4½ to 5 inches.
*Stem.*—Strong; stiff; upright.
*Form.*—Decorative.
*Petalage.*—Double.
*Color.*—Center of flower—Orange Chrome, Plate 2, lightly overcast with Flame Scarlet, Plate 2. Outer petals—Orange Buff, Plate 3. Base of petals—Glass Green, Plate 31. Inside of petals—Deep Chrome, Plate 3, lightly overcast with Mikado Orange, Plate 3. Reverse of petals—Light Orange Yellow, Plate 3.
*Petals.*—Texture—stiff. Form—oval.
*Fragrance.*—Characteristic chrysanthemum.

*Plant*

Form: Low.
Growth: Compact.
Foliage:
*Size.*—Medium.
*Quantity.*—Medium.
*Color.*—Upper side—Dark Cress Green, Plate 31. Under side—Rainette Green, Plate 31.
*Texture.*—Leathery.

I claim:

A new and distinct variety of chrysanthemum plant of the decorative class, substantially as herein shown and described, characterized particularly as to novelty by the unique combination of a low and compact habit of growth, a floriferous habit, an early blooming habit, a habit of blooming continuously, and a distinctive orange general color tonality of the bloom.

No references cited.